United States Patent [19]

Hoppe et al.

[11] Patent Number: 4,921,694

[45] Date of Patent: May 1, 1990

[54] DEODORIZING AND ANTIMICROBIAL COMPOSITION FOR USE IN COSMETIC OR TOPICAL FORMULATIONS

[75] Inventors: Udo Hoppe; Ulrich Eigener, both of Hamburg; Gerhard Sauermann, Wiemersdorf; Walter Engel, Pinneberg; Wolfgang Pape, Hamburg, all of Fed. Rep. of Germany

[73] Assignee: Beiersdorf Aktiengesellschaft, Hamburg, Fed. Rep. of Germany

[21] Appl. No.: 197,949

[22] Filed: May 24, 1988

[30] Foreign Application Priority Data

Jun. 24, 1987 [DE] Fed. Rep. of Germany ....... 3720831
Nov. 27, 1987 [DE] Fed. Rep. of Germany ....... 3740186

[51] Int. Cl.$^5$ .................. A61K 7/32; A61K 7/46; A61K 7/50; A61K 9/12
[52] U.S. Cl. ..................... 424/65; 252/106; 252/107; 424/DIG. 5; 424/47
[58] Field of Search ........................... 424/65

[56] References Cited

U.S. PATENT DOCUMENTS 2,451,149  10/1948  Boehm ........................... 514/718

FOREIGN PATENT DOCUMENTS 1642057  4/1971  Fed. Rep. of Germany ...... 252/106
2728921  1/1979  Fed. Rep. of Germany ........ 424/70
3315058  6/1985  Fed. Rep. of Germany ........ 424/65
1155789  6/1969  United Kingdom ................ 252/106

OTHER PUBLICATIONS

"Lexikon der Hilfsstoffe fur Pharmazie, Kosmetik und Agrenzende Gebiete", vol. 9, 1981, p. 439.

Primary Examiner—Dale R. Ore
Attorney, Agent, or Firm—Sprung Horn Kramer & Woods

[57] ABSTRACT

The invention relates to a deodorizing and antimicrobial composition for use in cosmetic or topical formulations which contains one or more 3,7,11-trimethyl-2,6,10-dodecatrien-1-ols, a phenyl hydroxyalkyl ether with not more than 3 C atoms in the alkyl radical and glycerol monolaurate.

6 Claims, No Drawings

DEODORIZING AND ANTIMICROBIAL COMPOSITION FOR USE IN COSMETIC OR TOPICAL FORMULATIONS

The invention relates to a deodorizing and antimicrobial composition for use in cosmetic or topical formulations, in particular deodorizing cosmetic agents.

Deodorizing cosmetic agents are used in particular to suppress unpleasant body odour which forms by the action of certain skin bacteria under the influence of heat and moisture on the initially largely odourless apocrine perspiration as a result of the formation of highly odiferous decomposition products.

As well as molecules which absorb odours, two main classes of products are currently known for combating bad odours resulting from perspiration.

On the one hand, antiperspirants are known which are based on products which suppress or greatly inhibit the formation of perspiration, such as astringents based on aluminium salts and in particular based on aluminium hydroxychloride. The formation of bad odours can be suppressed with these agents by suppressing their immediate cause, that is to say the development of perspiration by the epidermis (compare German Offenlegungsschrift 2,137,926). In contrast to these antiperspirants, cosmetic agents with a deodorizing action are a class of agents which although they have only a weak effect, if any, on the volume of perspiration, because of their bactericidal action they destroy the bacteria which lead to decomposition of the perspiration. These include agents with a content of antimicrobial substances. Amongst the compounds with such properties, there have been disclosed, for example, phenol derivatives with and without halogen substituents, organic mercury compounds, quaternary ammonium compounds, such as Cequartyl®, or certain ion exchangers or metal chelates of 1,3-diketones and amino acid derivatives with a disinfecting action.

Phenyl hydroxyalkyl ethers, in particular the compound known by the name phenoxyethanol, have furthermore been used as preservatives on the basis of their bactericidal and fungicidal actions on a number of microorganisms. Phenoxyethanol is active above all in an acid and neutral medium, and also in an alkaline medium, and is completely non-toxic. It already provides adequate protection in low concentrations. Because of its neutral taste, it rapidly found acceptance in the pharmaceutical and cosmetic industries. Nevertheless, its action is directed chiefly only towards Gram-negative bacteria.

From the chemical point of view, phenoxyethanol

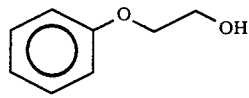

empirical formula: $C_8H_{10}O_2$
molecular weight: 138.17
is largely inert when used. It is a colourless, slightly viscous liquid with a weak, pleasant smell and an astringent taste, and is miscible with acetone, ethyl alcohol and glycerol, and soluble in water (1:45) and fats, for example olive oil and groundnut oil (1:50).

However, the solubility of phenoxyethanol in water is low and is not sufficient for some preservative purposes.

Phenoxyethanol, which is adequately described in the literature, has been detected in nature in tropical fruits, in *Cichorium endivia* and in green tea (*Camellia sinesis*). It has a mild, rose-like fragrance and is also used as a fixative for perfume compositions.

It is also known from British Patent Specification 1,155,789 that certain phenyl ethers can be used as antibacterial agents in cleansing compositions for the skin. Substituted phenyl ethers are also used as antibacterial agents (compare Offenlegungsschrift 1,642,057).

In a further development of the principle described above, attempts have therefore been made additionally to use the antimicrobial properties of certain odiferous substances, essential oils or other perfume constituents and to employ these as antimicrobial and deodorizing active compounds in deodorizing perfume compositions. German Offenlegungsschrift 2,728,921 and German Offenlegungsschrift 3,315,058 describe the natural substance farnesol (2-trans-6-trans-3,7,11-trimethyl-dodeca-2,5,10-trien-1-ol) and its 3 synthetic isomers as such an antimicrobially active substance which greatly inhibits the growth of odour-forming bacteria on the skin without greatly changing the entire bacterial flora of the skin. A disadvantage here is, however, that these compounds must be employed in considerably higher concentrations when used as a deodorizing antimicrobial active compound than in customary perfume compositions, in order to achieve the desired deodorizing effect.

Thus, for example, for complete inhibition of growth of the Gram-positive bacteria *Staphylococcus aureus* and *Staphylococcus epidermidis* and for substantial inhibition of Corynebacterium spec., a concentration of 0.3% by weight of farnesol, based on the cosmetic composition, is required. The content of farnesol in odiferous compositions and in deodorizing products is 0.2 to 0.5%.

Farnesol

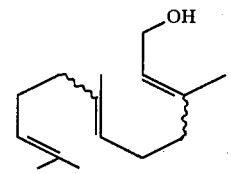

3,7,11-trimethyldodeca-2,5,10-trienol
empirical formula: $C_{15}H_{26}O$
molecular weight: 222.36
is an acyclic primary sesquiterpene alcohol, the natural occurrence of which has been adequately documented in the literature. Thus, it is found in Lemon-grass oil, palm-arosa oil, citronella oil, tuberose flower oil, sandalwood oil, linden flower oil, and in many other natural substances.

It is a colourless liquid with a typical odour and is clearly soluble in 3 parts of ethyl alcohol (70%).

Glycerol monolaurate, known by the trade name Lauricidin®, is also to be regarded as a germicide suitable for cosmetic agents. It is dispersible in water, soluble in alcohol, fats and paraffin oil, and miscible with acetone.

Glycerol monolaurate

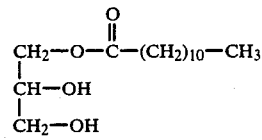

Empirical formula: $C_{15}H_{30}O_4$
Molecular weight: 274.41

Glycerol monolaurate has been detected in nature at least as a metabolism product in the digestion of edible fats. Various monoglycerides are therefore common as additives in the foodstuffs industry. Glycerol monolaurate itself is used as a pharmaceutical ointment base, as a coemulsifier for emulsions, and as a consistency-imparting component for the most diverse cosmetic agents, such as shampoo, bath additives, creams or lotions.

These two classes of agents described, however, are not completely satisfactory, because, on the one hand, the astringent agents or antiperspirants suppress the natural phenomenon of perspiration and moreover have an adverse effect on the epidermis, and, on the other hand, some of the bactericidal agents have the disadvantage that they completely destroy the microbial flora of the skin and accordingly substantially disturb the biological equilibrium of the epidermis.

Furthermore, the majority of these agents have a slightly phenolic odour. For this reason, there have been continuing efforts to prepare cosmetic agents which have a very good deodorizing action and a neutral odour and are free from side effects.

Deodorants which dispense with the traditional active compounds listed have indeed recently become known. For example, attempts have been made to solve the deodorant problem exclusively via the perfume. The body odour components are thereby said to be neutralized in the form of a fragrance complex of the perfume such that the disadvantageous body odour is masked for some time.

However, the action of these deodorizing cosmetic agents is inadequate for the requirements of practice in respect of action potency (masking of odour) and duration of action.

The antibacterial properties of certain odiferous substances, essential oils or other perfume constituents are furthermore used individually or as a mixture by manufacturing deodorizing perfume compositions as such. Products of this type have a deodorizing effect over a relatively long period of time both via the fragrance and via the antibacterial action.

Finally, there should also be mentioned a group of substances which prevent, via enzyme inhibition, unpleasantly smelling decomposition products from forming from the contents of perspiration, residues of horny skin and grease of the skin surface.

However, even if the risk of skin irritation is not caused to the same degree when deodorants are used as when antiperspirants are used, continuous use of deodorants also sometimes causes intolerances, photosensitivity and toxic side effects of varying intensity.

A frequent disadvantage of such deodorizing active compounds is that not only are the bacteria responsible for the body odour prevented from growing or destroyed, but moreover other bacteria of the bacterial skin flora are destroyed. Such deodorizing active compounds thus undesirably have a considerably more potent action than would be necessary to avoid body odour.

The following conditions are therefore linked with a satisfactory deodorant:

(1) preservation of the natural biology of the skin
(2) fragrance neutrality
(3) effectiveness only in respect of deodorization, that is to say only avoidance of and/or elimination of body odour
(4) avoidance of the formation of resistant strains of bacteria
(5) avoidance of the so-called accumulation effect
(6) innocuousness in the event of overdose or other use not as specified
(7) good cosmetic use and performance
(8) easy handling (for example as a liquid) and universal applicability in the most diverse cosmetic and external formulations
(9) excellent skin and mucous membrane tolerability
(10) use of non-polluting substances
(11) return to natural systems or substances which occur in nature with status (GRAS, RFM, and the like), and
(12) buffer capacity.

The object of the invention was thus to provide a deodorizing and antimicrobial composition based on starting substances which occur in nature or are close to nature, such as, for example, essential oils or fragrances, which effectively deodorizes with the maximum possible preservation of the natural biology of the skin, can be used universally in the most diverse deodorizing cosmetic agents and thereby requires smaller use quantities than provided by the previous prior art.

It has been found and the achievement of this object is that a composition of one or more 3,7,11-trimethyl-2,6,10-dodecatrien-1-ols, a phenyl hydroxyalkyl ether with not more than 3 C atoms in the alkyl radical and glycerol monolaurate meets the above requirements.

The invention thus relates to a deodorizing and antimicrobial composition for use in cosmetic or topical formulations, characterized in that it contains, based on the total amount of the formulation, (a) 15–45, preferably 32–36, % by weight of one or more 3,7,11-trimethyl-2,6,10-dodecatrien-1-ols,
(b) 30–70, preferably 51–55, % by weight of a phenylhydroxyalkyl ether with not more than 3 C atoms in the alkyl radical, and
(c) 5–25, preferably 9–15, % by weight of glycerol monolaurate, the amounts being chosen so that the sum of a), b) and c) gives 100%.

The various 3,7,11-trimethyl-2,6,10-dodecatrien-1-ols, that is to say the natural substance farnesol and its geometric isomers, can thereby be used individually or in the form of any desired mixture.

The phenyl hydroxyalkyl ethers with not more than 3 C atoms in the alkyl radical which are used in the composition according to the invention are preferably those in which the hydroxyl group is in position 2 on the alkyl radical.

The use of phenoxyethanol (ethylene glycol monophenyl ether) is particularly preferred. The ethylene glycol monophenyl ethers are used in the deodorizing antimicrobial composition according to the invention in amounts of 30 to 70% by weight, preferably 51 to 55% by weight, individually or as a mixture.

Although certain antimicrobial properties are also known for ethylene glycol monophenyl ether (U.S. Pat.

No. 2,451,149) and glycerol monolaurate, the composition according to the invention has proved surprisingly and unpredictably to be significantly more effective than was to be expected for the sum of the individual components.

In microbial studies, a synergistic action of the composition according to the invention has been detected for several relevant germs in that the active amount of the composition according to the invention contained smaller amounts of the 3 components than was calculated on the basis of the minimum inhibitory concentrations. Details in this respect are shown in Table 1. As described in detail in Example 1, the synergistic action was confirmed with the aid of the so-called Toxi-Chromo-test.

The deodorizing and antimicrobial composition according to the invention is thus also sufficiently effective at lower use quantities, compared with the individual components, when used in topical or cosmetic formulations.

A deodorizing effect can also in part be detected for compositions of the 3 components which lie outside the compositions claimed in claim 1. However, such compositions outside the ranges claimed prove to be unsuitable in practice, because the components can then no longer be mixed without problems and individual components tend to form separate phases, which leads to difficulties during incorporation into topical or cosmetic formulations. This particularly applies to high contents of glycerol monolaurate.

In contrast, a further advantage of the composition according to the invention is that it can be used without problems in the various types of formulations for deodorizing cosmetic agents, such as roll-on, stick, lotion, spray or solution.

Direct incorporation of the synergistic composition according to the invention into external compositions and cosmetic agents has the advantage that homogeneous distribution of the components is guaranteed and the time-consuming use of the individual components is thus excluded.

A preferred embodiment of the invention therefore provides deodorizing cosmetic agents which, in addition to the customary constituents, contain an effective amount of the composition according to the invention as the deodorizing active compound. Deodorizing cosmetic agents which preferably have a content of 0.05 to 5.00% by weight, in particular 0.10 to 0.9% by weight, based on the total amount of the cosmetic agent of the deodorizing and antimicrobial composition according to the invention, have therefore been found to be particularly advantageous in this embodiment of the invention.

Chemiluminescence measurements on the skin suggest that the good deodorizing action of the composition according to the invention is also to be attributed to oxidative reactions induced by the composition according to the invention, in addition to the antimicrobial action.

Another advantageous embodiment of the invention is the use of the deodorizing and antimicrobial composition according to the invention as an antimicrobial active compound for stabilizing topical or cosmetic formulations against decomposition by microorganisms.

The microbiological studies carried out (contact growth index according to Heiss) were performed with the bacteria species Staphylococcus aureus ATCC 6538 P, Staphylococcus epidermidis ATCC 12228, E. coli ATCC 8739, Pseudomonas aeruginosa ATCC 9027 and Propionibacterium acnes ATCC 6917. In each case, concentrations of 0.1, 0.3 and 1.0% of the compounds glycerol monolaurate (G), farnesol (F) and phenoxyethanol (P) were thereby brought together individually and as a mixture with a suspension of the test organisms ($10^8$–$10^9$ colony-forming units (CFU)/ml). The investigation was carried out in the customary manner, in that leaves of filter paper with an area of 23.8 cm$^2$ were each charged with 0.4 g of in each case a 0.1, 0.3 and 1.0% strength solution of the compounds (F), (G) and (P) and mixtures thereof. After drying of the solutions applied, the leaves of filter-paper were embedded in the nutrient agar in Petri dishes, the surface being covered with a thin nutrient agar layer. The plate was then inoculated with the test bacteria (compare Table 1).

The growth-inhibiting action by the test substances or mixtures thereof was evaluated with the aid of numbers 0 to 4, the index 4 indicating no action at all and no growth (total inhibiting action) being detectable with number 0. The letter D indicates that, in addition to the absence of growth in the region of the contact area of the filter leaf, virtually no growth is also to be detected in the edge region alongside the filter leaf, and an even better action than with the index 0 is thus present.

A clear antibacterial action against the 3 Gram-positive species of the 5 species of bacteria tested, which with these 3 species of bacteria resulted in total inhibition of growth, can thereby be detected for mixtures 1–7 in test concentrations of 1.0 and 0.3%.

Total to clear inhibition of growth is also detectable in the two Staphylococci strains at a use concentration of 0.1% of mixtures 1–7, whilst only slight inhibition by the mixtures 2, 3, 4 and 7 and no inhibition of growth by mixtures 1, 5 and 6 is detectable in *Propionibact. acnes* at this concentration.

This is surprising, since farnesol by itself is less active against the two Staphylococci when used in a concentration of 0.1% than, for example, mixtures 3, 5, 6 and 7, which contain only 15–34% of this compound. Glycerol monolaurate, which has a comparable action to the mixtures mentioned, is contained in these mixtures, however, in amounts of only 10–25%. Phenoxyethanol shows an action neither on *Staph. aureus* nor on *Staph. epidermidis*.

The pronounced action of the mixtures on *Propionibact. acnes* is also surprising, since farnesol and phenoxyethanol show virtually no action against this test germ as individual substances and glycerol monolaurate is used in the mixtures in an amount of only 5–25%. Precisely this activity is of the greatest importance, since this group of bacteria in particular chiefly causes odour formation in perspiration.

TABLE 1

Contact growth index (CGI) of glycerol monolaurate (G), farnesol (F) and phenoxyethanol (P) and mixtures thereof

| Test substance or mixture | Concentration used % | Use | Staph. aureus | Staph. epidermidis | Contact growth index Propionibact. acnes | Ps. aeruginosa | E. coli |
|---|---|---|---|---|---|---|---|
| Glycerol monolaurate | 1.0 | 0.4 g/ | D | D | 0 | 4 | 4 |

TABLE 1-continued

Contact growth index (CGI) of glycerol monolaurate (G), farnesol (F) and phenoxyethanol (P) and mixtures thereof

| Test substance or mixture | Concentration used % | Use | Staph. aureus | Staph. epidermidis | Contact growth index Propionibact. acnes | Ps. aeruginosa | E. coli |
|---|---|---|---|---|---|---|---|
|  | 0.3 | 23,8 cm² | D | D | 0 | 4 | 4 |
|  | 0.1 |  | 0 | 0 | 2 | 4 | 4 |
| Farnesol | 1.0 | 0.4 g/ | 0 | 0 | 3 | 4 | 4 |
|  | 0.3 | 23,8 cm² | 0 | 0 | 4 | 4 | 4 |
|  | 0.1 |  | 1 | 2 | 4 | 4 | 4 |
| Phenoxyethanol | 1.0 | 0.4 g/ | 4 | 4 | 4 | 4 | 4 |
|  | 0.3 | 23,8 cm² | 4 | 4 | 4 | 4 | 4 |
|  | 0.1 |  | 4 | 4 | 4 | 4 | 4 |
| Mixture 1 (G = 5% F = 45% P = 50%) | 1.0 | 0.4 g/ | 0 | 0 | D | 4 | 4 |
|  | 0.3 | 23,8 cm² | 0 | 0 | 0 | 4 | 4 |
|  | 0.1 |  | 1 | 1 | 4 | 4 | 4 |
| Mixture 2 (G = 10% F = 35% P = 55%) | 1.0 | 0.4 g/ | D | D | 0 | 4 | 4 |
|  | 0.3 | 23,8 cm² | 0 | 0 | 0 | 4 | 4 |
|  | 0.1 |  | 0 | 1 | 3 | 4 | 4 |
| Mixture 3 (G = 10% F = 30% P = 60%) | 1.0 | 0.4 g/ | D | D | D | 4 | 4 |
|  | 0.3 | 23,8 cm² | 0 | 0 | D | 4 | 4 |
|  | 0.1 |  | 0 | 0 | 3 | 4 | 4 |
| Mixture 4 (G = 10% F = 20% P = 70%) | 1.0 | 0.4 g/ | D | 0 | D | 4 | 4 |
|  | 0.3 | 23,8 cm² | 0 | 0 | D | 4 | 4 |
|  | 0.1 |  | 1 | 1 | 3 | 4 | 4 |
| Mixture 5 (G = 13% F = 34% P = 53%) | 1.0 | 0.4 g/ | D | D | D | 4 | 4 |
|  | 0.3 | 23,8 cm² | 0 | 0 | D | 4 | 4 |
|  | 0.1 |  | 0 | 0 | 4 | 4 | 4 |
| Mixture 6 (G = 15% F = 15% P = 70%) | 1.0 | 0.4 g/ | D | D | D | 4 | 4 |
|  | 0.3 | 23,8 cm² | 0 | 0 | D | 4 | 4 |
|  | 0.1 |  | 0 | 0 | 4 | 4 | 4 |
| Mixture 7 (G = 25% F = 25% P = 50%) | 1.0 | 0.4 g/ | D | D | D | 4 | 4 |
|  | 0.3 | 23,8 cm² | 0 | D | D | 4 | 4 |
|  | 0.1 |  | 0 | 0 | 2 | 4 | 4 |

EXAMPLE 1

The following mixture was brought together in a dissolving kettle with stirring equipment and was stirred at room temperature until a homogeneous solution had formed:
3,7,11-trimethyl-2,6,10-dodecatrien-1-ol (isomer mixture of 4 isomers, farnesol No. 2/027040 from Dragoco, Holzminden): 34 PW
phenoxyethanol: 53 PW
glycerol monolaurate: 13 PW The antimicrobial activity of the abovementioned composition according to the invention was investigated in comparison with the individual components with the aid of the Toxi-Chromotest (Orgenics Ltd., Yavne, Israel). The substances were used as 1% strength solutions or dispersions in water in dilution series. A solution of mercury chloride (4 mg/l) served as a control, and sodium lauryl sulphate (1 g/l) served as the internal standard. The minimum growth inhibition concentrations shown in rable 2 resulted against the E. coli mutants used for the test.

TABLE 2

| Test substance | Minimum inhibitory concentrations |
|---|---|
| mercury chloride | 0.05 ppm |
| glycerol monolaurate | 9.8 ppm |
| 3,7,11-trimethyl-2,6,10-dodecatrien-1-ol (isomer mixture of all 4 isomers) | 156.3 ppm |
| phenoxyethanol | 10,000.0 ppm |
| composition according to the invention | 39.1 ppm |
| sodium lauryl sulphate | 62.5 ppm |

Table 3 summarizes the concentrations of the individual components contained in the composition according to the invention and indicates the percentage of the minimum inhibitory concentration of each individual component which the composition according to the invention contains at the concentration which effects complete inhibition.

TABLE 3

| Substance | Concentration in the composition according to the invention for complete inhibition | % of the minimum inhibitory concentration of the individual substance |
|---|---|---|
| glycerol monolaurate | 5.1 ppm | 51.9% |
| 3,7,11-trimethyl-2,6,10-dodecatrien-1-ol | 13.3 ppm | 8.5% |
| phenoxyethanol | 20.7 ppm | 0.2% |
|  | total | 60.6% |

This shows that the active amount of the composition according to the invention contains all the components in concentrations which are below the minimum inhibitory concentration of the particular component. If the percentage concentrations of each component in the maximum inhibitory concentration are added up, a value which is clearly below the 100% which would be expected with additive behaviour of the components is obtained.

The composition according to the invention thus has a synergistic interaction, that is to say the components mutually intensify each other in their action.

The deodorizing cosmetic agents described in Examples 2 to 9 were prepared by the processes known to the expert and customary for the particular agents. The abbreviation PW denotes parts by weight and the abbreviation EO stands for ethylene oxide units.

EXAMPLE 2

Roll-on deodorant

Methylcellulose (Viskontran ® HEC 30 000): 0.80 PW

Water: 52.00 PW
Ethoxylated glycerol monococoate 7 EO (Cetiol® HE): 1.00 PW
Hydrogenated castor oil 40 EO (Cremophor® RH40): 2.50 PW
Ethanol: 39.20 PW
1,2-Propylene glycol: 3.00 PW
Perfume: 1.00 PW
Composition according to the invention from Example 1: 0.15 PW
0.025% strength colouring solution: 0.35 PW

EXAMPLE 3

Deodorizing stick 1,2-Propylene glycol: 46.00 PW
Stearic acid: 7.00 PW
Ethyl alcohol: 35.10 PW
Water: 10.00 PW
NaOH lozenges: 1.20 PW
Perfume: 0.50 PW
Composition according to the invention from Example 1: 0.20 PW

EXAMPLE 4

Deodorizing lotion (viscous)

Polyethylene glycol(20) oleyl ether (Cremophor®O): 2.00 PW
Cetylstearyl alcohol: 3.00 PW
Paraffin oil: 5.00 PW
1,2-Propylene glycol: 3.00 PW
Polyvinylpyrrolidone (Luviskol® K30): 0.50 PW
Composition according to the invention from Example 1: 0.15 PW
Water: 89.90 PW
Perfume: 0.45 PW

EXAMPLE 5

Deodorizing lotion (thin)

Ethoxylated fatty alcohol 6 EO (Cremophor® A): 1.00 PW
Polyethylene glycol(20) oleyl ether (Cremophor®O): 1.00 PW
Glycerol monostearate: 2.00 PW
Cetyl alcohol: 1.00 PW
Isopropyl myristate: 2.00 Pw
Glycerol: 1.00 PW
Polyvinylpyrrolidone (Luviskol® K30): 0.50 PW
Composition according to the invention from Example 1: 0.15 PW
Water: 90.90 PW
Perfume: 0.45 PW

EXAMPLE 6

Deodorizing pump spray (not aerosol)

Ethanol: 61.50 PW
Ethoxylated glycerol monococoate 7 EO (Cetiol® HE): 1.50 PW
Composition according to the invention from Example 1: 0.40 PW
Citric acid: 0.02 PW
Water: 36.18 PW

EXAMPLE 7

Deodorizing body spray (aerosol)

Ethanol: 21.35 PW
1,2-Propylene glycol: 3.00 PW
Octyldodecanol (Eutanol® G): 0.04 PW
Perfume: 0.50 PW
Composition according to the invention from Example 1: 0.10 PW
Isopropyl myristate: 0.01 PW
Propellant gas: 75.00 PW

EXAMPLE 8

Deodorizing intimate washing solution

30% strength cocoamidopropyl-betain (Tego-Betain® L7): 10.00 PW
Ethoxylated glycerol monolaurate 22 EO (Tagat® L2): 2.00 PW
Composition according to the invention from Example 1: 0.10 PW
80% strength lactic acid: 0.50 PW
Perfume: 0.08 PW
Water: 87.32 PW

EXAMPLE 9

Deodorizing agent (liquid) against hair odour

Polyethylene glycol 400: 0.20 PW
Ethanol: 37.50 PW
Perfume: 0.10 PW
Composition according to the invention from Example 1: 0.10 PW
Hydrogenated castor oil 40 EO (Cremophor® RH 40): 0.20 PW
Citric acid: 0.01 PW
Water: 61.89 PW

EXAMPLE 10

| Deodorizing soap | |
|---|---|
| Basic soap 80/20 (about 78% of fatty acid) | 96.84 PW |
| Superfatting agent | 1.45 PW |
| Dyestuffs | 0.01 PW |
| Antioxidant | 0.05 PW |
| Perfume | 1.07 PW |
| Titanium dioxide | 0.19 PW |
| Composition according to the invention from Example 1 | 0.39 PW |
| | 100.00 PW |

We claim:

1. A synergistic deodorizing and antibacterial composition consisting essentially of, based on the total amount of the composition of
   (a) 32–36% by weight of at least one 3,7,11-trimethyl-2,6,10-dodecatrien-1-ol,
   (b) 51–55% by weight of a phenoxyethanol, and
   (c) 9–15% by weight of glycerol monolaurate.

2. A composition according to claim 1, consisting essentially of
   (a) 34% by weight of at least one 3,7,11-trimethyl-2,6,10-dodecatrien-1-ol,
   (b) 53% by weight of phenoxyethanol, and
   (c) 13% by weight of glycerol monolaurate.

3. A deodorizing cosmetic composition comprising a cosmetic base and an effective amount of a composition according to claim 1.

4. A deodorizing cosmetic composition comprising a cosmetic base and 0.05 to 5% by weight of a composition according to claim 1.

5. A method of stabilizing a topical or cosmetic composition against decomposition by microorganisms which comprises incorporating therein a composition according to claim 1.

6. The method according to claim 5, wherein the composition is incorporated in the topical or cosmetic composition in from about 0.5 to 8% by weight.

* * * * *